US005776750A

United States Patent [19]
Hodgson et al.

[11] Patent Number: 5,776,750
[45] Date of Patent: Jul. 7, 1998

[54] ALANYL TRNA SYNTHETASE POLYNUCLEOYIDES OF STAPHLOCOCCUS

[75] Inventors: John Edward Hodgson; Elizabeth Jane Lawlor, both of Malvern, Pa.

[73] Assignee: Smithkline Beecham p.l.c., Brentford, England

[21] Appl. No.: 785,071

[22] Filed: Jan. 17, 1997

[30] Foreign Application Priority Data

Jan. 19, 1996 [GB] United Kingdom .................. 9601099
Oct. 30, 1996 [GB] United Kingdom .................. 9622617

[51] Int. Cl.$^6$ .................. C12N 9/00; C12N 15/00; C12N 1/20; C07H 21/04
[52] U.S. Cl. .................. 435/183; 435/6; 435/252.3; 435/254.11; 435/325; 435/320.1; 536/23.2; 536/24.3
[58] Field of Search .................. 435/6, 183, 252.3, 435/254.11, 320.1, 325; 536/23.2, 24.3

[56] References Cited

U.S. PATENT DOCUMENTS 5,561,054  10/1996  Kron et al. ............... 435/69.1

FOREIGN PATENT DOCUMENTS

WO 94/28139  12/1994  WIPO.
WO 95/09927  4/1995  WIPO.

OTHER PUBLICATIONS

Chang et al. (1990) Primary Structure of Alanyl–tRNA Synthetase and the Regulation of its mRNA Levels in *Bombyx mori*. J. Biol. Chem. 265 (34): 20898–20906.

Kron et al., "An immundominant antigen in *Brugia malayi* is an asparaginyl–tRNA synthetase", *Febs Letters*, 374 pp. 122–124 (1995).

Chalker, et al., "Analysis and toxic overexpression in *Escherichia coli* of a staphylococcal gene encoding isoleucyl–tRNA synthetase", *Gene*, 141, pp. 103–108 (1994).

Nilsen, et al., "Cloning and characterization of a potentially protective antigen in lymphatic filariasis", *Proc. Natl. Acad. Sci. USA*, 85, pp. 3604–3607 (1988).

Fraser, et al., The Minimal Gene Complement of *Mycoplasma genitalium*, *Science*, 270, pp. 397–403 (1995).

Putney, et al., "Cloning, Partial sequencing, and *in Vitro* Transcription of the Gene for Alanine tRNA Synthetase", *The Journal of Biochemical Chemistry*, 256, No. 1, pp. 205–211 (1981).

Fleischmann, et al., "Whole–Genome Sequencing and Assembly of Haemophilus Influenzae Rd", *Science*, 269, pp. 496–512 (1995) and *EMBL Sequence Database*, Accession No. L42093.

*Primary Examiner*—Robert A. Wax
*Assistant Examiner*—Lisa J. Hobbs
*Attorney, Agent, or Firm*—Edward R. Gimmi; William T. Han; Edward T. Lentz

[57] ABSTRACT

The invention provides tRNA synthetase polypeptides and DNA (RNA) encoding tRNA synthetase polypetides and methods for producing such polypeptides by recombinant techniques. Also provided are methods for utilizing tRNA synthetase polypeptide for the protection against infection, particularly bacterial infections.

27 Claims, 8 Drawing Sheets

Alanyl tRNA synthetase cloned DNA sequence [SEQ ID NO:1]

```
  1  ATGAAAAAGT TAAAAGCGAG TGAAATTAGA CAAAAATATC TAGATTTCTT
 51  TGTTGAAAAA GGACATATGG TTGAACCTTC TGCACCATTA GTGCCAATTG
101  ATGATGATAC ATTATTATGG ATTAATTCAG GTGTAGCAAC ATTAAAGAAA
151  TATTTTGATG GACGTGAAAC ACCTAAAAAG ATATTGAAAA TAAACTCTCA
201  AAAAGCTATT CGTACAAATG CTTTGAAAAT TGTTGGTTTC ACAGCGCGTC
251  ACCATACATT CTTTGAAATG TTAGGTAACT TCTCAATTGG TGATTATTTT
301  AAACAAGAAG CGATTGAATT TGCTTGGGAA TTTTTAACGA GTGATAAATG
351  GATGGGTATG GAGCCAGATA AATTGTACGT TACGATTCAT CCGGAAGATA
401  TGGAAGCATA TAACATTTGG CATAAAGATA TTGGGCTTGA AGAAAGTCGT
```

FIG. 1

| | | | | | |
|---|---|---|---|---|---|
| 451 | ATTATTCGCA | TTGAAGGTAA | CTTCTGGGAT | ATTGGTGAAG | GGCCTTCAGG |
| 501 | ACCGAACACT | GAGATTTTCT | ATGATCGCGG | AGAAGCATAT | GGACAAGACG |
| 551 | ATCCGGCAGA | AGAAATGTAT | CCAGGTGGAG | AAAATGAACG | CTATCTTGAA |
| 601 | GTATGGAACT | TAGTATTTAG | TGAATTCAAT | CATAATAAAG | ATCATAGTTA |
| 651 | CACACCATTA | CCTAATAAAA | ATATTGATAC | CGGCATGGGG | CTTGAGCGTA |
| 701 | TGGCCTCAGT | TTCTCAAAAT | GTACGTACTA | ACTATGAAAC | AGATTTATTT |
| 751 | ATGCCTATAA | TGAATGAAAT | CGAAAAAGTA | TCAGGTAAAC | AATATTTAGT |
| 801 | AAACAACGAA | CAAGATGTGG | CATTTAAAGT | AATTGCTGAC | CACATTCGTA |
| 851 | CGATTGCATT | TGCAATTTCT | GATGGTGCAT | TACCTGCCAA | TGAAGGTAGA |

FIG. 1A

```
 901  GGATATGTAT TACGTCGATT GTTACGTCGT GCCGTTCGTT TTAGTCAAAC
 951  GTTAGGAATC AATGAGCCAT TTATGTACAA ACTTGTTGAT ATTGTTGCAG
1001  ACATTATGGA ACCATATTAT CCAAATGTTA AGGAAAAAGC AGATTTCATT
1051  AAGCGTGTTA TAAAGTCTGA AGAAGAACGA TTCCATGAAA CATTAGAAGA
1101  TGGTTTAGCG ATTTTAAATG AATTAATTAA AAAAGCTAAA GCGACAACAA
1151  ATGAAATTAA TGGGAAAGAT GCATTTAAAT TGTATGATAC GTACGGGTTC
1201  CCAATTGAAT TAACTGAAGA AATAGCAGTG CAAGCAGGAT TGAAAGTTGA
1251  TATGACAACA TTTGAGTCAG AAATGCAACA ACAACGTGAT CGTGCACGTC
1301  AAGCACGTCA AAATTCTCAA TCAATGCAAG TTCAAAGTGA AGTATTGAAA
```

FIG. 1B

```
1351 AATATTACAT CTGCAAGTAC TTTTGTTGGT TATGATACTG CGACAGCTCA
1401 AACAACACTA ACACACTTGA TATATAATGG TGAAGAAGTT TCACAAGTTG
1451 AAGCGGGTGA AACAGTATAC TTCATGTTAA CGGAAACACC ATTTTATGCA
1501 GTCAGTGGTG GACAAGTTGC GGATACAGGT ATTGTTTATA ATGACAATTT
1551 TGAAATTGCT GTTAGTGAAG TAACCAAAGC ACCAAATGGT CAAAACTTGC
1601 ATAAAGGAGT AGTACAATTT GGCCAAGTAA ATGTTGGCGC TACAGTGTCT
1651 GCTGAAGTGA ACCAAAATGA TCGACGTGAC ATTCAAAAGA ACCATAGTGC
1701 AACACATTTA TTACATGCAG CGTTGAAATC AGTACTGGGT GATCATGTTA
1751 ACCAAGCTGG TTCACTAGTA GAAGCAGATC GTTTACGTTT TGATTTCTCT
```

FIG. 1C

```
1801 CATTTTGGTC CAATGACTAA TGATGAAATT GATCAAGTTG AACGCTTAGT

1851 AAATGAAGAA ATTTGGAAAG GTATTGACGT TAACATTCAA GAAATGGATA

1901 TTGCTTCAGC TAAAGAAATG GGCGCAATGG CATTATTCGG TGAAAAATAT

1951 GGTGATGTTG TGCGTGTAGT AAATATGGCA CCATTTTCAA TTGAATTATG

2001 TGGTGGTATT CATGTCCGCA ATACTTCTGA AATTGGCTTA TTCAAAATAG

2051 TAAGTGAGTC AGGTACAGGA GCTGGTGTGC GTCGTATTGA AGCATTAACA

2101 GGTAAAGCAG CTTTCTTATA TTTAGAAGAT ATTCAAGAGA AATTTAATAC

2151 GATGAAATCA CAGATGAAAG TGAAATCTGA TGATCAAGTA GTCGAAAAGT

2201 TAACACAATT ACAAGATGAA GAAAAAGCAT TATTAAAACA ATTAGAGCAA
```

FIG. 1D

```
2251 CGTGACAAAG AAATCACATC ACTTAAAATG GGTAATATTG AAGATCAAGT

2301 TGAAGAAATC AATGGCTATA AAGTATTGGT TACTGAAGTG GATGTACCAA

2351 ATGCGAAAGC AATTCGCTCG ACAATGGATG ATTTTAAATC TAAACTACAA

2401 GATACAATTA TCATTCTTGC AAGTAATGTT GATGATAAAG TATCGATGGT

2451 TGCAACTGTC CCTAAATCTT TAACAAATAA CGTTAAAGCC GGTGATCTTA

2501 TCAAACAAAT GGCACCAATC GTTGGTGGTA AAGGTGGCGG TCGTCCAGAT

2551 ATGGCTCAAG GTGGCGGGTAC ACAACCTGAA AATATCTCAA AATCATTAAG

2601 CTTTATTAAA GATTACATTA AAAATCTATA A
```

FIG. 1E

Alanyl tRNA synthetase deduced amino acid sequence [SEQ ID NO:2]

```
  1  MKKLKASEIR QKYLDFFVEK GHMVEPSAPL VPIDDDTLLW INSGVATLKK

51  YFDGRETPKK PRIVNSQKAI RTNDIENVGF TARHHTFFEM LGNFSIGDYF

101  KQEAIEFAWE FLTSDKWMGM EPDKLYVTIH PEDMEAYNIW HKDIGLEESR

151  IIRIEGNFWD IGEGPSGPNT EIFYDRGEAY GQDDPAEEMY PGGENERYLE

201  VWNLVFSEFN HNKDHSYTPL PNKNIDTGMG LERMASVSQN VRTNYETDLF

251  MPIMNEIEKV SGKQYLVNNE QDVAFKVIAD HIRTIAFAIS DGALPANEGR

301  GYVLRRLLRR AVRFSQTLGI NEPFMYKLVD IVADIMEPYY PNVKEKADFI

351  KRVIKSEEER FHETLEDGLA ILNELIKKAK ATTNEINGKD AFKLYDTYGF

401  PIELTEEIAV QAGLKVDMTT FESEMQQQRD RARQARQNSQ SMQVQSEVLK
```

FIG. 2

```
451  NITSASTFVG YDTATAQTTL THLIYNGEEV SQVEAGETVY FMLTETPFYA
501  VSGGQVADTG IVYNDNFEIA VSEVTKAPNG QNLHKGVVQF GQVNVGATVS
551  AEVNQNDRRD IQKNHSATHL LHAALKSVLG DHVNQAGSLV EADRLRFDFS
601  HFGPMTNDEI DQVERLVNEE IWKGIDVNIQ EMDIASAKEM GAMALFGEKY
651  GDVVRVVNMA PFSIELCGGI HVRNTSEIGL FKIVSESGTG AGVRRIEALT
701  GKAAFLYLED IQEKFNTMKS QMKVKSDDQV VEKLTQLQDE EKALLKQLEQ
751  RDKEITSLKM GNIEDQVEEI NGYKVLVTEV DVPNAKAIRS TMDDFKSKLQ
801  DTIILASNV DDKVSMVATV PKSLTNNVKA GDLIKQMAPI VGGKGGGRPD
851  MAQGGGTQPE NISKSLSFIK DYIKNL
```

FIG. 2A

ALANYL TRNA SYNTHETASE POLYNUCLEOYIDES OF STAPHLOCOCCUS

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the tRNA synthetase family hereinafter referred to as "tRNA synthetase".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. S. aureus is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The tRNA synthetases have a primary role in protein synthesis according to the following scheme:

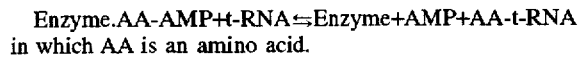

in which AA is an amino acid.

Inhibition of this process leads to a reduction in the levels of charged tRNA and this triggers a cascade of responses known as the stringent response, the result of which is the induction of a state of dormancy in the organism. As such selective inhibitors of bacterial tRNA synthetase have potential as antibacterial agents. One example of such is mupirocin which is a selective inhibitor of isoleucyl tRNA synthetase. Isolation of tRNA synthetase allows for the identification and analysis of potential antibacterial targets to facilitate screening for antibacterial compounds. Isoleucyl tRNA synthetase, isolated from Staphylococcus aureus, has already been described (Chalker, A., F., Ward, J., M., Fosberry, A., P. and Hodgson, J., E. 1994 Gene 141:103–108).

Clearly, there is a need for factors that may be used to screen compounds for antibiotic activity and which factors may also be used to determine their roles in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known Escherichia coli alanyl tRNA synthetase protein.

SUMMARY OF THE INVENTION

It is an object of the invention to provide polypeptides that have been identified as novel tRNA synthetase polypeptides by homology between the amino acid sequence set out in FIG. 2 and a known amino acid sequence or sequences of other proteins such as Escherichia coli alanyl tRNA synthetase protein.

It is a further object of the invention to provide polynucleotides that encode tRNA synthetase polypeptides, particularly polynucleotides that encode the polypeptide herein designated tRNA synthetase.

In a particularly preferred embodiment of this aspect of the invention the polynucleotide comprises a region encoding alanyl tRNA synthetase polypeptides comprising the sequence set out in FIG. 1 [SEQ ID NO:1], or a variant thereof.

In another particularly preferred embodiment of the invention there is a novel alanyl tRNA synthetase protein from Staphylococcus aureus comprising the amino acid sequence of FIG. 2 [SEQ ID NO:2], or a variant thereof.

In accordance with this aspect of the invention there is provided an isolated nucleic acid molecule encoding a mature polypeptide expressible by the Staphylococcus aureus WCUH 29 strain contained in NCIMB Deposit No. 40771.

In accordance with this aspect of the invention there are provided isolated nucleic acid molecules encoding tRNA synthetase, particularly Staphylococcus aureus tRNA synthetase, including mRNAs, cDNAs, genomic DNAs. Further embodiments of this aspect of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of this aspect of the invention are naturally occurring allelic variants of tRNA synthetase and polypeptides encoded thereby.

In accordance with this aspect of the invention there are provided novel polypeptides of Staphylococcus aureus referred to herein as tRNA synthetase as well as biologically, diagnostically, prophylactically, clinically or therapeutically useful variants thereof, and compositions comprising the same.

Among the particularly preferred embodiments of this aspect of the invention are variants of tRNA synthetase polypeptide encoded by naturally occurring alleles of the tRNA synthetase gene.

In a preferred embodiment of this aspect of the invention there are provided methods for producing the aforementioned tRNA synthetase polypeptides.

In accordance with yet another aspect of the invention, there are provided inhibitors to such polypeptides, useful as antibacterial agents, including, for example, antibodies.

In accordance with certain preferred embodiments of this aspect of the invention, there are provided products, compositions and methods for (i) assessing tRNA synthetase expression, (ii) treating disease, for example, disease, such as, infections of the upper respiratory tract (e.g., otitis media, bacterial tracheitis, acute epigiottitis, thyroiditis), lower respiratory (e.g., empyema, lung abscess), cardiac (e.g., infective endocarditis), gastrointestinal (e.g., secretory diarrhea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis), (iii) assaying genetic variation, (iv) and administering a tRNA synthetase polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to tRNA synthetase polynucleotide sequences, particularly under stringent conditions.

In certain preferred embodiments of this aspect of the invention there are provided antibodies against tRNA synthetase polypeptides.

In accordance with another aspect of the invention, there are provided tRNA synthetase agonists and antagonists each of which are also preferably bacteriostatic or bacteriocidal.

In a further aspect of the invention there are provided compositions comprising a tRNA synthetase polynucleotide or a tRNA synthetase polypeptide for administration to a cell or to a multicellular organism.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

The following drawings depict certain embodiments of the invention They are illustrative only and do not limit the invention otherwise disclosed herein.

FIG. 1 (and A, B, C, D and E) shows the polynucleotide sequence of *Staphylococcus aureus* alanyl tRNA synthetase [SEQ ID NO:1].

FIG. 2 (and A) shows the amino acid sequence of *Staphylococcus aureus* alanyl tRNA synthetase [SEQ ID NO:2] deduced from the polynucleotide sequence of FIG. 1.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods (*Computational Molecular Biology*, Lesk, A. M., ed., Oxford University Press. New York. 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991). While there exist a number of methods to measure identity and similarity between two sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Methods commonly employed to determine identity or similarity between sequences include, but are not limited to those disclosed in Carillo, H., and Lipman, D., SIAM *J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215:403–410 (1990)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215:403–410 (1990)). "Isolated" means altered "by the hand of man" from its natural state, i.e., if it occurs in nature, it has been changed or removed from its original environment, or both. For example, polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide (s)" includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques which are well known to the art. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains and the amino or carboxyl termini. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663:48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel tRNA synthetase polypeptides and polynucleotides as described in greater detail below. In particular, the invention relates to polypeptides and polynucleotides of a novel tRNA synthetase gene of *Staphylococcus aureus*, which is related by amino acid sequence homology to *Escherichia coli* alanyl tRNA synthetase polypeptide. The invention relates especially to tRNA synthetase having the nucleotide and amino acid sequences set out in FIG. 1 and FIG. 2 respectively, and to the tRNA synthetase nucleotide sequences of the DNA in NCIMB Deposit No. 40771 and amino acid sequences encoded thereby.

Techniques are available to evaluate temporal gene expression in bacteria, particularly as it applies to viability under laboratory and host infection conditions. A number of methods can be used to identify genes which are essential to survival per se, or essential to the establishment and/or maintenance of an infection. Identification of expression of a sequence by one of these methods yields additional information about its function and assists in the selection of such sequence for further development as a screening target. Briefly, these approaches include for example;

1) Signature Tagged Mutagenesis (STM)

This technique is described by Hensel et al., *Science* 269:400–403(1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

In *Staphylococcus aureus*, because the transposon system is less well developed, a more efficient way of creating the tagged mutants is to use the insertion-duplication mutagenesis technique as described by Morrison et al., *J. Bacteriol.* 159:870 (1984) the contents of which is incorporated by reference for background purposes.

2) In Vivo Expression Technology (IVET)

This technique is described by Camilli et al., *Proc. Nat'l. Acad. Sci. USA.* 91:2634–2638 (1994) and Mahan et al., *Infectious Agents and Diseases* 2:263–268 (1994), the contents of each of which is incorporated by reference for background purposes. IVET identifies genes up-regulated during infection when compared to laboratory cultivation, implying an important role in infection. Sequences identified by this technique are implied to have a significant role in infection establishment/maintenance.

In this technique random chromosomal fragments of target organism are cloned upstream of a promoter-less reporter gene in a plasmid vector. The pool is introduced into a host and at various times after infection bacteria may be recovered and assessed for the presence of reporter gene expression. The chromosomal fragment carried upstream of an expressed reporter gene should carry a promoter or portion of a gene normally upregulated during infection. Sequencing upstream of the reporter gene allows identification of the up regulated gene.

3) Differential display

This technique is described by Chuang et al., *J. Bacteriol.* 175:2026–2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of conditional lethal mutants by transposon mutagenesis

This technique, described by de Lorenzo, V. et al., *Gene* 123:17–24 (1993); Neuwald, A. F. et al., *Gene* 125:69–73 (1993); and Takiff, Ho E. et al., *J. Bacteriol.* 174:1544–1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of conditional lethal mutants by chemical mutagenesis

This technique is described by Beckwith, J., *Methods in Enzymology* 204:3–18 (1991), the contents of which are incorporated herein by reference for background purposes. In this technique random chemical mutagenesis of target organism, growth at temperature other than physiological temperature (permissive temperature) and subsequent replica plating and growth at different temperature (e.g., 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antibacterials developed to cure established and chronic infections.

6) RT-PCR

Bacterial messenger RNA, preferably that of *Staphylococcus aureus*, is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of bacterial 16S ribosomal RNA, preferably that of *Staphylococcus aureus*, as detected by probing Northerns with a suitably labeled sequence specific oligonucleotide probe. Typically, a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Use of the of these technologies when applied to the sequences of the invention enables identification of bacterial proteins expressed during infection, inhibitors of which would have utility in anti-bacterial therapy Deposited materials A deposit containing a *Staphylococcus aureus* WCUH 29 strain has been deposited with the National Collections of Industrial and Marine Bacteria Ltd. (NCIMB), 23 St. Machar Drive, Aberdeen AB2 1RY, Scotland on 11 Sep. 1995 and assigned NCIMB Deposit No. 40771. The *Staphylococcus aureus* strain deposit is referred to herein as "the deposited strain" or as "the DNA of the deposited strain."

The deposited material is a strain that contains the full length tRNA synthetase DNA, referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112.

A license may be required to make, use or sell the deposited materials, and no such license is hereby granted.

Polypeptides

The polypeptides of the invention include the polypeptide of FIG. 2 [SEQ ID NO:2] (in particular the mature polypeptide) as well as polypeptides and fragments, particularly those which have the biological activity of tRNA synthetase, and also those which have at least 70% identity to the polypeptide of FIG. 2 [SEQ ID NO:2] or the relevant portion, preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

Variants that are fragments of the polypeptides of the invention may be employed for producing the corresponding full-length polypeptide by peptide synthesis; therefore, these variants may be employed as intermediates for producing the full-length polypeptides. Variants that are fragments of the polynucleotides of the invention may be used to synthesize full-length polynucleotides of the invention.

A fragment is a variant polypeptide having an amino acid sequence that entirely is the same as part but not all of the amino acid sequence of the aforementioned polypeptides. As with tRNA synthetase polypeptides fragments may be "free-standing," or comprised within a larger polypeptide of which they form a part or region, most preferably as a single continuous region, a single larger polypeptide.

Preferred fragments include, for example, truncation polypeptides having a portion of the amino acid sequence of FIG. 2 [SEQ ID NO:2], or of variants thereof, except for deletion of a continuous series of residues that includes the amino terminus, or a continuous series of residues that includes the carboxyl terminus or deletion of two continuous series of residues, one including the amino terminus and one including the carboxyl terminus. Degradation forms of the polypeptides of the invention in a host cell, particularly a Staphylococcus aureus, are also preferred. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of tRNA synthetase, including those with a similar activity or an improved activity, or with a decreased undesirable activity. Also included are those fragments that are antigenic or immunogenic in an animal, especially in a human.

Polynucleotides

Another aspect of the invention relates to isolated polynucleotides which encode the tRNA synthetase polypeptide having the deduced amino acid sequence of FIG. 2 [SEQ ID NO:2] and polynucleotides closely related thereto and variants thereto.

Using the information provided herein, such as the polynucleotide sequence set out in FIG. 1 [SEQ ID NO:1], a polynucleotide of the invention encoding tRNA synthetase polypeptide may be obtained using standard cloning and screening, such as those for cloning and sequencing chromosomal DNA fragments from Staphylococcus aureus WCUH 29 cells as starting material, followed by obtaining a full length clone. For example, to obtain a polynucleotide sequence of the invention, such as that sequence given in FIG. 1 [SEQ ID NO:1], typically a library of clones of chromosomal DNA of Staphylococcus aureus WCUH 29 in E.coli or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in FIG. 1 [SEQ ID NO:1] was discovered in a DNA library derived from Staphylococcus aureus WCUH 29.

The DNA sequence thus obtained is set out in FIG. 1 [SEQ ID NO:1]. It contains an open reading frame encoding a protein having about the number of amino acid residues set forth in FIG. 2 [SEQ ID NO:2] with a deduced molecular weight that can be calculated using amino acid residue molecular weight values well known in the art. Novel tRNA synthetase of the invention is structurally related to other proteins of the tRNA synthetase family, as shown by the results of sequencing the DNA encoding tRNA synthetase of the deposited strain. The protein exhibits greatest homology to Escherichia coli alanyl tRNA synthetase protein among known proteins. tRNA synthetase of FIG. 2 [SEQ ID NO:2] has about 46% identity over its entire length and about 67% similarity over its entire length with the amino acid sequence of Escherichia coli alanyl tRNA synthetase polypeptide.

Sequence of the invention may also be identical over its entire length to the coding sequence in FIG. 1 [SEQ ID NO:1].

Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of this aspect of the invention, the marker sequence is a hexa-histidine peptide, as provided in the pQE vector (Qiagen, Inc.) and described in Gentz et al., Proc. Natl. Acad. Sci., USA 86:821–824 (1989), or an HA tag (Wilson et al., Cell 37:767 (1984)). Polynucleotides of the invention also include, but are not limited to, polynucleotides comprising a structural gene and its naturally associated sequences that control gene expression.

In accordance with the foregoing, the term "polynucleotide encoding a polypeptide" as used herein encompasses polynucleotides which include a sequence encoding a polypeptide of the invention, particularly bacterial, and more particularly the Staphylococcus aureus tRNA synthetase having the amino acid sequence set out in FIG. 2 [SEQ ID NO:2]. The term encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the herein above described polynucleotides which encode for variants of the polypeptide having the deduced amino acid sequence of FIG. 2 [SEQ ID NO:2].

Further particularly preferred embodiments are polynucleotides encoding tRNA synthetase variants, which have the amino acid sequence of tRNA synthetase polypeptide of FIG. 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of tRNA synthetase.

Further preferred embodiments of the invention are polynucleotides that are at least 70% identical over their entire length to a polynucleotide encoding tRNA synthetase polypeptide having the amino acid sequence set out in FIG. 2 [SEQ ID NO:2], and polynucleotides which are complementary to such polynucleotides. Alternatively, most highly preferred are polynucleotides that comprise a region that is at least 80% identical over their entire length to a polynucleotide encoding tRNA synthetase polypeptide of the *Staphylococcus aureus* DNA of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of FIG. 1 [SEQ ID NO:1].

The invention further relates to polynucleotides that hybridize to the herein above-described sequences. In this regard, the invention especially relates to polynucleotides which hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

The invention also provides a polynucleotide consisting essentially of a polynucleotide sequence obtainable by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate fulllength cDNAs and genomic clones encoding tRNA synthetase and to isolate cDNA and genomic clones of other genes that have a high sequence similarity to the tRNA synthetase gene. Such probes generally will comprise at least 15 bases. Preferably, such probes will have at least 30 bases and may have at least 50 bases. Particularly preferred probes will have at least 30 bases and will have 50 bases or less.

For example, the coding region of the tRNA synthetase gene may be isolated by screening using the known DNA sequence to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed as research reagents and materials for discovery of treatments of and diagnostics for disease, particularly human disease, as further discussed herein relating to polynucleotide assays, inter alia.

Polynucleotides of the invention that are oligonucleotides derived from the sequences of SEQ ID NOS:1 and 2 may be used in the processes herein as described, but preferably for PCR, to determine whether or not the polynucleotides identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxylterminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Vectors, host cells, expression

The invention also relates to vectors which comprise a polynucleotide or polynucleotides of the invention, host cells which are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the tRNA synthetase polynucleotides of the invention for use as diagnostic reagents. Detection of tRNA synthetase in a eukaryote, particularly a mammal, and especially a human, will provide a diagnostic method for diagnosis of a disease. Eukaryotes (herein also "individual(s)"), particularly mammals, and especially humans, infected with an organism comprising the tRNA synthetase gene may be detected at the DNA level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the strain of prokaryote present in a eukaryote, particularly a mammal, and especially a human, may be made by an analysis of the genotype of the prokaryote gene. Deletions and insertions can be detected by a change in size of the amplified product in comparison to the genotype of a reference sequence. Point mutations can be identified by hybridizing amplified DNA to labeled tRNA synthetase polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., Science, 230:1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85:4397-4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding tRNA synthetase can be used to identify and analyze mutations. These primers may be used for amplifying tRNA synthetase DNA isolated from a sample derived from an individual. The invention also provides these primers with 1, 2, 3 or 4 nucleotides removed from the 5' and/or the 3' end. The primers may be used to amplify the gene isolated from an infected individual such that the gene may then be subject to various techniques for elucidation of the DNA sequence. In this way, mutations in the DNA sequence may be detected and used to diagnose infection and to serotype or classify the infectious agent.

The invention provides a process for diagnosing, disease, preferably bacterial infections, more preferably infections by Staphylococcus aureus, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of FIG.

1 [SEQ ID NO:1]. Increased or decreased expression of tRNA synthetase polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of tRNA synthetase protein compared to normal control tissue samples may be used to detect the presence of an infection, for example. Assay techniques that can be used to determine levels of a tRNA synthetase protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art which provides antibodies produced by continuous cell line cultures can be used. Examples include various techniques, such as those in Kohler, G. and Milstein, C., Nature 256:495–497 (1975); Kozbor et al., Immunology Today 4:72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against tRNA synthetase may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis), and bone and joint (e.g., septic arthritis, osteomyelitis).

Polypeptide variants include antigenically, epitopically or immunologically equivalent variants which form a particular aspect of this invention. The term "antigenically equivalent derivative" as used herein encompasses a polypeptide or its equivalent which will be specifically recognised by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

Antagonists and agonists—assays and molecules

The invention also provides a method of screening compounds to identify those which enhance (agonist) or block (antagonist) the action of tRNA synthetase polypeptides or polynucleotides.

For example, to screen for agonists or antagonists, a synthetic reaction mix, a cellular compartment, such as a membrane, cell envelope or cell wall, or a preparation of any thereof, comprising tRNA synthetase polypeptide and a labeled substrate or ligand of such polypeptide is incubated in the absence or the presence of a candidate molecule which may be a tRNA synthetase agonist or antagonist. The ability of the candidate molecule to agonize or antagonize the tRNA synthetase polypeptide is reflected in decreased binding of the labeled ligand or decreased production of product from such substrate. Molecules which bind gratuitously, i.e., without inducing the effects of tRNA synthetase are most likely to be good antagonists. Molecules that bind well and increase the rate of product production from substrate are agonists. The rate or level of production of product from substrate may be enhanced by using a reporter system. Reporter systems that may be useful in this regard include but are not limited to calorimetric labeled substrate converted into product, a reporter gene that is responsive to changes in tRNA synthetase activity, and binding assays known in the art.

Another example of an assay for tRNA synthetase antagonists is a competitive assay that combines tRNA synthetase and a potential antagonist with tRNA synthetase-binding molecules, recombinant tRNA synthetase binding molecules, natural substrates or ligands, or substrate or ligand mimetics, under appropriate conditions for a competitive inhibition assay. tRNA synthetase can be labeled, such as by radioactivity or a calorimetric compound, such that the number of tRNA synthetase molecules bound to a binding molecule or converted to product can be determined accurately to assess the effectiveness of the potential antagonist.

In a further aspect, this invention provides a method of screening drugs to identify those which interfere with the interaction of the novel tRNA synthetase of the invention. The enzyme mediated incorporation of radiolabelled amino acid into tRNA may be measured by the aminoacylation method which measures amino acid-tRNA as trichloroacetic acid-precipitable radioactivity from radiolabelled amino acid in the presence of tRNA and ATP (Hughes J., Mellows G. and Soughton S., 1980, FEBS Letters, 122:322–324). Thus inhibitors of tRNA synthetase of the invention can be detected by a reduction in the trichloroacetic acid precipitable radioactivity relative to the control. Alternatively, novel tRNA synthetase catalysed partial PPi/ATP exchange reaction which measures the formation of radiolabelled ATP from PPi can be used to detect novel tRNA synthetase inhibitors (Calender R & Berg P, 1966, Biochemistry, 5, 1681–1690).

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing tRNA synthetase-induced activities, thereby preventing the action of tRNA synthetase by excluding tRNA synthetase from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56:560 (1991); OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of tRNA synthetase.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block tRNA synthetase protein mediated mammalian cell invasion by, for example, initiating phosphorylation of mammalian tyrosine kinases (Rosenshine et al., Infect. Immun. 60:2211 (1992); iii) to block bacterial adhesion between mammalian extracellular matrix proteins and bacterial tRNA synthetase proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed for instance to inhibit disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis), and bone and joint (e.g., septic arthritis, osteomyelitis).

Vaccines

Another aspect of the invention relates to a method for inducing an immunological response in an individual, particularly a mammal which comprises inoculating the individual with tRNA synthetase, or a fragment or variant thereof, adequate to produce antibody to protect said individual from infection, particularly bacterial infection and most particularly Staphylococcus aureus infections. Yet another aspect of the invention relates to a method of inducing immunological response in an individual which comprises, through gene therapy, delivering gene encoding tRNA synthetase, or a fragment or a variant thereof, for expressing tRNA synthetase, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a tRNA synthetase or protein coded therefrom, wherein the composition comprises a recombinant tRNA synthetase or protein coded therefrom comprising DNA which codes for and expresses an antigen of said tRNA synthetase or protein coded therefrom.

The tRNA synthetase or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273:352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infections, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insionic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain tRNA synthetase, it is to be understood that this covers fragments of the naturally occurring protein and similar proteins with additions, deletions or substitutions which do not substantially affect the immunogenic properties of the recombinant protein.

Compositions, kits and administration

The invention also relates to compositions comprising the polynucleotide or the polypeptides discussed above or the agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device.

Treatment may be continued after surgery during the in-body time of the device. In addition, the composition could also be used to broaden perioperative cover for any surgical technique to prevent bacterial wound infections, especially *Staphylococcus aureus* wound infections Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 μg/kg of antigen, and such dose is preferably administered 1–3 times and with an interval of 1–3 weeks. With the indicated dose range, no adverse toxicological effects will be observed with the compounds of the invention which would preclude their administration to suitable individuals.

The antibodies described above may also be used as diagnostic reagents to detect the presence of bacteria containing the tRNA synthetase protein.

EXAMPLES

The examples below are carried out using standard techniques, which are well known and routine to those of skill in the art, except where otherwise described in detail. The examples are illustrative, but do not limit the invention.

Example 1

Library Production

The polynucleotide having the DNA sequence given in SEQ ID NO:1 was obtained from a library of clones of chromosomal DNA of *Staphylococcus aureus* in *E. coli*. In some cases the sequencing data from two or more clones containing overlapping *Staphylococcus aureus* DNAs was used to construct the contiguous DNA sequence in SEQ ID NO: 1. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bsh1235I), and such fragments are size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

Example 2

Measurement of Alanyl tRNA Synthetase (ARS) Activity.

The enzyme catalyses the aminoacylation of tRNAAla, which proceeds through a two step mechanism. The first step involves the formation of a stable enzyme:alanyl adenylate complex resulting from the specific binding and reaction of ATP and L-alanine. Subsequently, the 3' terminal adenosine of enzyme-bound tRNAAla reacts with the aminoacyladenylate, leading to the esterification of the tRNA and release of AMP. These steps are summarised below;

a) L-Ala+ATP.Mg+ARS→ARS:Ala-AMP+PPi.Mg b) ARS:Ala-AMP+tRNAAla→ARS+Ala-tRNAAla+AMP

This reaction can be assayed in order to characterise the enzyme or identify specific inhibitors of its activity in a number of ways:

Measurement of the formation of Ala-tRNAAla can be specifically determined using radiolabelled alanine and separating free alanine from Ala-tRNA using precipitation/filtration techniques (e.g. in cold trichloroacetic acid[1,2])

The full acylation reaction can also be measured by analysing production of either PPi or AMP which are produced in stoichiometric ratio to the tRNA acylation. This may be achieved in a number of ways for example using colorimetric[3]; or enzyme coupled[4] measurement of Pi after addition of excess inorganic pyrophosphatase or using enzyme coupled assays to directly measure AMP or PPi production[5]. The partial reaction (a) can be assayed through radiolabel isotopic exchange between ATP and PPi, since each of the steps in this part of the reaction are freely reversible. This typically has a kcat around 20-fold higher than the full acylation reaction (a+b), and is readily measured using chromatographic principles which separate PPi from ATP (i.e. using activated charcoaled[1,2].

Ligand Binding to ARS

It is also possible to define ligand interactions with ARS in experiments that are not dependent upon enzyme catalysed turnover of substrates. This type of experiment can be done in a number of ways:

Effects of ligand binding upon enzyme intrinsic fluorescence (e.g. of tryptophan). Binding of either natural ligands or inhibitors may result in enzyme conformational changes which alter enzyme fluorescence. Using stopped-flow fluorescence equipment, this can be used to define the microscopic rate constants that describe binding. Alternatively, steady-state fluorescence titration methods can yield the overall dissociation constant for binding in the same way that these are accessed through enzyme inhibition experiments Spectral effects of ligands. Where the ligands themselves are either fluorescent or possess chromophores that overlap with enzyme tryptophan fluorescence, binding can be detected either via changes in the ligand fluorescence properties (e.g. intensity, lifetime or polarisation) or fluorescence resonance energy transfer with enzyme tryptophans. The ligands could either be inhibitors or variants of the natural ligands (i.e. fluorescent ATP derivatives or tRNAAla labelled with a fluorophore).

Thermal analysis of the enzyme:ligand complex. Using calorimetric techniques (e.g. Isothermal Calorimetry, Differential Scanning Calorimetry) it is possible to detect thermal changes, or shifts in the stability of ARS which reports and therefore allows the characterisation of ligand binding.

REFERENCES

1. Calender & Berg (1966) Biochemistry 5, 1681–1690
2. Toth M. J. & Schimmel P. (1990) J. Biol. Chem. 265, 1000–1004
3. Hoenig (1989) J. Biochem. Biophys. Meth. 19, 249–252
4. Webb T. M. (1994) Anal. Biochem. 218, 449–454
5. Sigma Chemicals Catalogue, 1986

Example 3
Aminoacylation Assays for ARS Activity

Assays are performed either using purified S. aureus ARS overexpressed in E. coli, or using crude cell lysate from E. coli overexpressing ARS. The latter usually contains around 10% of total protein as ARS. Enzyme is stored at −70° C. in 50 mM Tris-HCl buffer (pH 7.8), 10 mM $MgCl_2$ and 10 mM B-mercaptoethanol after flash freezing in liquid $N_2$. In experiments to determine the activity of enzyme samples, these stocks are diluted over a wide range (100 fold to 10,000 fold) in 50 mM Tris pH 7.8, 10 mM $MgCl_2$, 1 mM Dithiothreitol and stored on ice prior to assay.

The assay procedure is as follows; 50 ml of enzyme prepared and diluted as described above is mixed with reaction mixture (100 ml), comprising: 0.25 uCi L-[U-14C]-Alanine (Amersham International), 4 mg/ml E. coli MRE600 mixed tRNA (from Boehringer Manheim), 5 mM ATP, 15 mM $MgSO_4$, 3 mM DTr, 75 mM KCl and 50 mM Tris-HCl pH 7.8. Unless otherwise stated, all reagents are obtained from Sigma Chemical Company Ltd. Concentrations are given as in the final reaction mix. After addition of the enzyme to start the reaction, assay samples are incubated at 37° C. and, at the desired time, duplicate aliquots (50 ul) are removed and quenched with 7% trichloroacetic acid (100 ul) and left on ice for 30 min. The precipitates are harvested using a Packard Filtermate 196 Cell Harvester [Packard Instruments Ltd.] onto glass fibre filters which are washed successively with 7% trichloroacetic acid and ethanol. The filters are dried at 70° C. for 1 hour and the levels of radioactivity measured by scintillation counting (Packard Topcount).

---

What is claimed is:

1. An isolated polynucleotide comprising a polynucleotide sequence selected from the group consisting of:
   (a) a polynucleotide having at least a 95% identity to a polynucleotide encoding a polypeptide comprising the amino acid sequence of SEQ ID NO:2;
   (b) a polynucleotide having at least a 97% identity to a polynucleotide encoding a polypeptide comprising the amino acid sequence of SEQ ID NO:2;
   (c) a polynucleotide encoding a polypeptide comprising the amino acid sequence of SEQ ID NO:2;
   (d) a polynucleotide hybridizing under stringent conditions to a polynucleotide encoding a polypeptide comprising the amino acid sequence of SEQ ID NO:2;
   (e) a polynucleotide having at least a 95% identity to a polynucleotide encoding the same mature polypeptide expressed by the alanyl tRNA synthetase gene contained in NCIMB Deposit No. 40771;
   (f) a polynucleotide having at least a 97% identity to a polynucleotide encoding the same mature polypeptide expressed by the alanyl tRNA synthetase gene contained in NCIMB Deposit No. 40171;
   (g) a polynucleotide encoding the same mature polypeptide expressed by the alanyl tRNA synthetase gene contained in NCIMB Deposit No. 40771;
   (h) a polynucleotide which is complementary to the polynucleotide of (a), (b), (c), (d), (e), (f) or (g).

2. The isolated polynucleotide of claim 1 wherein said polynucleotide is a polynucleotide having at least a 95% identity to a polynucleotide encoding a polypeptide comprising the amino acid sequence of SEQ ID NO:2.

3. The isolated polynucleotide of claim 1 wherein said polynucleotide is a polynucleotide having at least a 97% identity to a polynucleotide encoding a polypeptide comprising the amino acid sequence of SEQ ID NO:2.

4. The isolated polynucleotide of claim 1 wherein said polynucleotide is a polynucleotide encoding a polypeptide comprising the amino acid sequence of SEQ ID NO:2.

5. The isolated polynucleotide of claim 1 wherein said polynucleotide is a polynucleotide hybridizing under stringent conditions to a polynucleotide encoding a polypeptide comprising the amino acid sequence of SEQ ID NO:2.

6. The isolated polynucleotide of claim 1 wherein said polynucleotide is a polynucleotide having at least a 95% identity to a polynucleotide encoding the same mature polypeptide expressed by the alanyl tRNA synthetase gene contained in NCIMB Deposit No. 40771.

7. The isolated polynucleotide of claim 1 wherein said polynucleotide is a polynucleotide having at least a 97% identity to a polynucleotide encoding the same mature polypeptide expressed by the alanyl tRNA synthetase gene contained in NCIMB Deposit No. 40771.

8. The isolated polynucleotide of claim 1 wherein said polynucleotide is a polynucleotide encoding the same mature polypeptide expressed by the alanyl tRNA synthetase gene contained in NCIMB Deposit No. 40771.

9. The polynucleotide of claim 1 wherein the polynucleotide is DNA.

10. The polynucleotide of claim 1 wherein the polynucleotide is RNA.

11. The polynucleotide of claim 4 wherein the polynucleotide is DNA.

12. The polynucleotide of claim 4 wherein the polynucleotide is RNA.

13. The polynucleotide of claim 4 comprising the nucleotides 1 to 2628 set forth in SEQ ID NO:1.

14. The polynucleotide of claim 4 which encodes the polypeptide consisting of SEQ ID NO:2.

15. A vector comprising the DNA of claim 4.

16. A host cell comprising the vector of claim 8.

17. A process for producing a polypeptide comprising: expressing from the host cell of claim 9 a polypeptide encoded by said DNA.

18. A process for producing a cell which expresses a polypeptide comprising transforming or transfecting the cell with the vector of claim 8 such that the cell expresses the polypeptide encoded by the DNA contained in the vector.

19. A process for producing a cell which expresses a polypeptide comprising transforming or transfecting the cell with the vector of claim 8 such that the cell expresses the polypeptide encoded by the DNA contained in the vector.

20. A process for producing a tRNA synthetase polypeptide or fragment, which fragment retains either or both of binding or catalytic activity, comprising culturing a host of claim 9 under conditions sufficient for the production of said polypeptide or fragment.

21. An isolated polynucleotide comprising the polynucleotide sequence set forth in SEQ ID NO:1.

22. An isolated polynucleotide comprising the nucleotides 1 to 2628 set forth in SEQ ID NO:1.

23. An isolated polynucleotide comprising the polynucleotide sequence set forth in SEQ ID NO:1.

24. An isolated polynucleotide consisting of the polynucleotide sequence set forth in SEQ ID NO:1.

25. An isolated polynucleotide consisting of the polynucleotide sequence encoding the polypeptide sequence set forth in SEQ ID NO:2.

26. An isolated polynucleotide comprising a DNA sequence obtained by screening an appropriate library containing the complete gene encoding an amino acid sequence set forth in SEQ ID NO:2 under stringent hybridization conditions with a probe having a polynucleotide sequence encoding the amino acid sequence set forth in SEQ ID NO:2 or a fragment thereof, which fragment retains either or both of binding or catalytic activity; and isolating said DNA sequence.

27. The isolated polynucleotide of claim 18 comprising of nucleotides 1 to 2628 set forth in SEQ ID NO:1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2631 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:1:

```
ATGAAAAAGT  TAAAAGCGAG  TGAAATTAGA  CAAAAATATC  TAGATTTCTT  TGTTGAAAAA   60
GGACATATGG  TTGAACCTTC  TGCACCATTA  GTGCCAATTG  ATGATGATAC  ATTATTATGG  120
ATTAATTCAG  GTGTAGCAAC  ATTAAAGAAA  TATTTTGATG  GACGTGAAAC  ACCTAAAAAG  180
CCAAGAATTG  TAAACTCTCA  AAAAGCTATT  CGTACAAATG  ATATTGAAAA  TGTTGGTTTC  240
ACAGCGCGTC  ACCATACATT  CTTTGAAATG  TTAGGTAACT  TCTCAATTGG  TGATTATTTT  300
AAACAAGAAG  CGATTGAATT  TGCTTGGGAA  TTTTTAACGA  GTGATAAATG  GATGGGTATG  360
GAGCCAGATA  AATTGTACGT  TACGATTCAT  CCGGAAGATA  TGGAAGCATA  TAACATTTGG  420
CATAAAGATA  TTGGGCTTGA  AGAAAGTCGT  ATTATTCGCA  TTGAAGGTAA  CTTCTGGGAT  480
ATTGGTGAAG  GGCCTTCAGG  ACCGAACACT  GAGATTTTCT  ATGATCGCGG  AGAAGCATAT  540
GGACAAGACG  ATCCGGCAGA  AGAAATGTAT  CCAGGTGGAG  AAAATGAACG  CTATCTTGAA  600
GTATGGAACT  TAGTATTTAG  TGAATTCAAT  CATAATAAAG  ATCATAGTTA  CACACCATTA  660
CCTAATAAAA  ATATTGATAC  CGGCATGGGG  CTTGAGCGTA  TGGCCTCAGT  TTCTCAAAAT  720
GTACGTACTA  ACTATGAAAC  AGATTTATTT  ATGCCTATAA  TGAATGAAAT  CGAAAAAGTA  780
TCAGGTAAAC  AATATTTAGT  AAACAACGAA  CAAGATGTGG  CATTTAAAGT  AATTGCTGAC  840
CACATTCGTA  CGATTGCATT  TGCAATTTCT  GATGGTGCAT  TACCTGCCAA  TGAAGGTAGA  900
```

```
GGATATGTAT  TACGTCGATT  GTTACGTCGT  GCCGTTCGTT  TTAGTCAAAC  GTTAGGAATC    960

AATGAGCCAT  TTATGTACAA  ACTTGTTGAT  ATTGTTGCAG  ACATTATGGA  ACCATATTAT   1020

CCAAATGTTA  AGGAAAAAGC  AGATTTCATT  AAGCGTGTTA  TAAAGTCTGA  AGAAGAACGA   1080

TTCCATGAAA  CATTAGAAGA  TGGTTTAGCG  ATTTTAAATG  AATTAATTAA  AAAAGCTAAA   1140

GCGACAACAA  ATGAAATTAA  TGGGAAAGAT  GCATTTAAAT  TGTATGATAC  GTACGGGTTC   1200

CCAATTGAAT  TAACTGAAGA  AATAGCAGTG  CAAGCAGGAT  TGAAAGTTGA  TATGACAACA   1260

TTTGAGTCAG  AAATGCAACA  ACAACGTGAT  CGTGCACGTC  AAGCACGTCA  AAATTCTCAA   1320

TCAATGCAAG  TTCAAAGTGA  AGTATTGAAA  AATATTACAT  CTGCAAGTAC  TTTTGTTGGT   1380

TATGATACTG  CGACAGCTCA  AACAACACTA  ACACACTTGA  TATATAATGG  TGAAGAAGTT   1440

TCACAAGTTG  AAGCGGGTGA  AACAGTATAC  TTCATGTTAA  CGGAACACC   ATTTTATGCA   1500

GTCAGTGGTG  GACAAGTTGC  GGATACAGGT  ATTGTTTATA  ATGACAATTT  TGAAATTGCT   1560

GTTAGTGAAG  TAACCAAAGC  ACCAAATGGT  CAAAACTTGC  ATAAAGGAGT  AGTACAATTT   1620

GGCCAAGTAA  ATGTTGGCGC  TACAGTGTCT  GCTGAAGTGA  ACCAAAATGA  TCGACGTGAC   1680

ATTCAAAAGA  ACCATAGTGC  AACACATTTA  TTACATGCAG  CGTTGAAATC  AGTACTGGGT   1740

GATCATGTTA  ACCAAGCTGG  TTCACTAGTA  GAAGCAGATC  GTTACGTTT   TGATTTCTCT   1800

CATTTTGGTC  AATGACTAA   TGATGAAATT  GATCAAGTTG  AACGCTTAGT  AAATGAAGAA   1860

ATTTGGAAAG  GTATTGACGT  TAACATTCAA  GAAATGGATA  TTGCTTCAGC  TAAAGAAATG   1920

GGCGCAATGG  CATTATTCGG  TGAAAAATAT  GGTGATGTTG  TGCGTGTAGT  AAATATGGCA   1980

CCATTTTCAA  TTGAATTATG  TGGTGGTATT  CATGTCCGCA  ATACTTCTGA  AATTGGCTTA   2040

TTCAAAATAG  TAAGTGAGTC  AGGTACAGGA  GCTGGTGTGC  GTCGTATTGA  AGCATTAACA   2100

GGTAAAGCAG  CTTTCTTATA  TTTAGAAGAT  ATTCAAGAGA  AATTTAATAC  GATGAAATCA   2160

CAGATGAAAG  TGAAATCTGA  TGATCAAGTA  GTCGAAAAGT  TAACACAATT  ACAAGATGAA   2220

GAAAAAGCAT  TATTAAAACA  ATTAGAGCAA  CGTGACAAAG  AAATCACATC  ACTTAAAATG   2280

GGTAATATTG  AAGATCAAGT  TGAAGAAATC  AATGGCTATA  AAGTATTGGT  TACTGAAGTG   2340

GATGTACCAA  ATGCGAAAGC  AATTCGCTCG  ACAATGGATG  ATTTTAAATC  TAAACTACAA   2400

GATACAATTA  TCATTCTTGC  AAGTAATGTT  GATGATAAAG  TATCGATGGT  TGCAACTGTC   2460

CCTAAATCTT  TAACAAATAA  CGTTAAAGCC  GGTGATCTTA  TCAAACAAAT  GGCACCAATC   2520

GTTGGTGGTA  AAGGTGGCGG  TCGTCCAGAT  ATGGCTCAAG  GTGGCGGTAC  ACAACCTGAA   2580

AATATCTCAA  AATCATTAAG  CTTTATTAAA  GATTACATTA  AAAATCTATA  A            2631
```

( 2 ) INFORMATION FOR SEQ ID NO:2:

( i ) SEQUENCE CHARACTERISTICS:
        ( A ) LENGTH: 876 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Lys  Lys  Leu  Lys  Ala  Ser  Glu  Ile  Arg  Gln  Lys  Tyr  Leu  Asp  Phe
 1                 5                      10                      15

Phe  Val  Glu  Lys  Gly  His  Met  Val  Glu  Pro  Ser  Ala  Pro  Leu  Val  Pro
           20                      25                      30

Ile  Asp  Asp  Asp  Thr  Leu  Leu  Trp  Ile  Asn  Ser  Gly  Val  Ala  Thr  Leu
                35                      40                      45
```

|     |     |     |     |     |     |     |     |     |     |     |     |     |     |     |
|-----|-----|-----|-----|-----|-----|-----|-----|-----|-----|-----|-----|-----|-----|-----|
| Lys | Lys 50 | Tyr | Phe | Asp | Gly 55 | Arg | Glu | Thr | Pro | Lys 60 | Lys | Pro | Arg | Ile | Val |
| Asn 65 | Ser | Gln | Lys | Ala | Ile 70 | Arg | Thr | Asn | Asp | Ile 75 | Glu | Asn | Val | Gly | Phe 80 |
| Thr | Ala | Arg | His | His 85 | Thr | Phe | Phe | Glu | Met 90 | Leu | Gly | Asn | Phe | Ser 95 | Ile |
| Gly | Asp | Tyr | Phe 100 | Lys | Gln | Glu | Ala | Ile 105 | Glu | Phe | Ala | Trp | Glu 110 | Phe | Leu |
| Thr | Ser | Asp 115 | Lys | Trp | Met | Gly 120 | Met | Glu | Pro | Asp | Lys 125 | Leu | Tyr | Val | Thr |
| Ile | His 130 | Pro | Glu | Asp | Met | Glu 135 | Ala | Tyr | Asn | Ile | Trp 140 | His | Lys | Asp | Ile |
| Gly 145 | Leu | Glu | Glu | Ser | Arg 150 | Ile | Ile | Arg | Ile | Glu 155 | Gly | Asn | Phe | Trp | Asp 160 |
| Ile | Gly | Glu | Gly | Pro 165 | Ser | Gly | Pro | Asn | Thr 170 | Glu | Ile | Phe | Tyr | Asp 175 | Arg |
| Gly | Glu | Ala | Tyr 180 | Gly | Gln | Asp | Asp | Pro 185 | Ala | Glu | Glu | Met | Tyr 190 | Pro | Gly |
| Gly | Glu | Asn 195 | Glu | Arg | Tyr | Leu | Glu 200 | Val | Trp | Asn | Leu | Val 205 | Phe | Ser | Glu |
| Phe | Asn 210 | His | Asn | Lys | Asp | His 215 | Ser | Tyr | Thr | Pro | Leu 220 | Pro | Asn | Lys | Asn |
| Ile 225 | Asp | Thr | Gly | Met | Gly 230 | Leu | Glu | Arg | Met | Ala 235 | Ser | Val | Ser | Gln | Asn 240 |
| Val | Arg | Thr | Asn | Tyr 245 | Glu | Thr | Asp | Leu | Phe 250 | Met | Pro | Ile | Met | Asn 255 | Glu |
| Ile | Glu | Lys | Val 260 | Ser | Gly | Lys | Gln | Tyr 265 | Leu | Val | Asn | Asn | Glu 270 | Gln | Asp |
| Val | Ala | Phe 275 | Lys | Val | Ile | Ala | Asp 280 | His | Ile | Arg | Thr | Ile 285 | Ala | Phe | Ala |
| Ile | Ser 290 | Asp | Gly | Ala | Leu | Pro 295 | Ala | Asn | Glu | Gly | Arg 300 | Gly | Tyr | Val | Leu |
| Arg 305 | Arg | Leu | Leu | Arg | Arg 310 | Ala | Val | Arg | Phe | Ser 315 | Gln | Thr | Leu | Gly | Ile 320 |
| Asn | Glu | Pro | Phe | Met 325 | Tyr | Lys | Leu | Val | Asp 330 | Ile | Val | Ala | Asp | Ile 335 | Met |
| Glu | Pro | Tyr | Tyr 340 | Pro | Asn | Val | Lys | Glu 345 | Lys | Ala | Asp | Phe | Ile 350 | Lys | Arg |
| Val | Ile | Lys 355 | Ser | Glu | Glu | Glu | Arg 360 | Phe | His | Glu | Thr | Leu 365 | Glu | Asp | Gly |
| Leu | Ala 370 | Ile | Leu | Asn | Glu | Leu 375 | Ile | Lys | Lys | Ala | Lys 380 | Ala | Thr | Thr | Asn |
| Glu 385 | Ile | Asn | Gly | Lys | Asp 390 | Ala | Phe | Lys | Leu | Tyr 395 | Asp | Thr | Tyr | Gly | Phe 400 |
| Pro | Ile | Glu | Leu | Thr 405 | Glu | Glu | Ile | Ala | Val 410 | Gln | Ala | Gly | Leu | Lys 415 | Val |
| Asp | Met | Thr | Thr 420 | Phe | Glu | Ser | Glu | Met 425 | Gln | Gln | Gln | Arg | Asp 430 | Arg | Ala |
| Arg | Gln | Ala 435 | Arg | Gln | Asn | Ser | Gln 440 | Ser | Met | Gln | Val | Gln 445 | Ser | Glu | Val |
| Leu | Lys 450 | Asn | Ile | Thr | Ser | Ala 455 | Ser | Thr | Phe | Val | Gly 460 | Tyr | Asp | Thr | Ala |
| Thr | Ala | Gln | Thr | Thr | Leu | Thr | His | Leu | Ile | Tyr | Asn | Gly | Glu | Glu | Val |

-continued

| 465 | | | | | 470 | | | | 475 | | | | 480 |
|---|---|---|---|---|---|---|---|---|---|---|---|---|---|
| Ser | Gln | Val | Glu | Ala | Gly | Glu | Thr | Val | Tyr | Phe | Met | Leu | Thr | Glu | Thr |
| | | | | 485 | | | | 490 | | | | 495 | |
| Pro | Phe | Tyr | Ala | Val | Ser | Gly | Gly | Gln | Val | Ala | Asp | Thr | Gly | Ile | Val |
| | | | 500 | | | | 505 | | | | 510 | | |
| Tyr | Asn | Asp | Asn | Phe | Glu | Ile | Ala | Val | Ser | Glu | Val | Thr | Lys | Ala | Pro |
| | | 515 | | | | 520 | | | | 525 | | | |
| Asn | Gly | Gln | Asn | Leu | His | Lys | Gly | Val | Val | Gln | Phe | Gly | Gln | Val | Asn |
| | 530 | | | | 535 | | | | 540 | | | | |
| Val | Gly | Ala | Thr | Val | Ser | Ala | Glu | Val | Asn | Gln | Asn | Asp | Arg | Arg | Asp |
| 545 | | | | 550 | | | | 555 | | | | 560 | |
| Ile | Gln | Lys | Asn | His | Ser | Ala | Thr | His | Leu | Leu | His | Ala | Ala | Leu | Lys |
| | | | 565 | | | | 570 | | | | 575 | | |
| Ser | Val | Leu | Gly | Asp | His | Val | Asn | Gln | Ala | Gly | Ser | Leu | Val | Glu | Ala |
| | | | 580 | | | | 585 | | | | 590 | | |
| Asp | Arg | Leu | Arg | Phe | Asp | Phe | Ser | His | Phe | Gly | Pro | Met | Thr | Asn | Asp |
| | | 595 | | | | 600 | | | | 605 | | | |
| Glu | Ile | Asp | Gln | Val | Glu | Arg | Leu | Val | Asn | Glu | Glu | Ile | Trp | Lys | Gly |
| | 610 | | | | 615 | | | | 620 | | | | |
| Ile | Asp | Val | Asn | Ile | Gln | Glu | Met | Asp | Ile | Ala | Ser | Ala | Lys | Glu | Met |
| 625 | | | | 630 | | | | 635 | | | | 640 | |
| Gly | Ala | Met | Ala | Leu | Phe | Gly | Glu | Lys | Tyr | Gly | Asp | Val | Val | Arg | Val |
| | | | 645 | | | | 650 | | | | 655 | | |
| Val | Asn | Met | Ala | Pro | Phe | Ser | Ile | Glu | Leu | Cys | Gly | Gly | Ile | His | Val |
| | | | 660 | | | | 665 | | | | 670 | | |
| Arg | Asn | Thr | Ser | Glu | Ile | Gly | Leu | Phe | Lys | Ile | Val | Ser | Glu | Ser | Gly |
| | | 675 | | | | 680 | | | | 685 | | | |
| Thr | Gly | Ala | Gly | Val | Arg | Arg | Ile | Glu | Ala | Leu | Thr | Gly | Lys | Ala | Ala |
| | 690 | | | | 695 | | | | 700 | | | | |
| Phe | Leu | Tyr | Leu | Glu | Asp | Ile | Gln | Glu | Lys | Phe | Asn | Thr | Met | Lys | Ser |
| 705 | | | | 710 | | | | 715 | | | | 720 | |
| Gln | Met | Lys | Val | Lys | Ser | Asp | Asp | Gln | Val | Val | Glu | Lys | Leu | Thr | Gln |
| | | | 725 | | | | 730 | | | | 735 | | |
| Leu | Gln | Asp | Glu | Glu | Lys | Ala | Leu | Leu | Lys | Gln | Leu | Glu | Gln | Arg | Asp |
| | | 740 | | | | 745 | | | | 750 | | | |
| Lys | Glu | Ile | Thr | Ser | Leu | Lys | Met | Gly | Asn | Ile | Glu | Asp | Gln | Val | Glu |
| | | 755 | | | | 760 | | | | 765 | | | |
| Glu | Ile | Asn | Gly | Tyr | Lys | Val | Leu | Val | Thr | Glu | Val | Asp | Val | Pro | Asn |
| | 770 | | | | 775 | | | | 780 | | | | |
| Ala | Lys | Ala | Ile | Arg | Ser | Thr | Met | Asp | Asp | Phe | Lys | Ser | Lys | Leu | Gln |
| 785 | | | | 790 | | | | 795 | | | | 800 | |
| Asp | Thr | Ile | Ile | Ile | Leu | Ala | Ser | Asn | Val | Asp | Asp | Lys | Val | Ser | Met |
| | | | 805 | | | | 810 | | | | 815 | | |
| Val | Ala | Thr | Val | Pro | Lys | Ser | Leu | Thr | Asn | Asn | Val | Lys | Ala | Gly | Asp |
| | | | 820 | | | | 825 | | | | 830 | | |
| Leu | Ile | Lys | Gln | Met | Ala | Pro | Ile | Val | Gly | Gly | Lys | Gly | Gly | Gly | Arg |
| | | 835 | | | | 840 | | | | 845 | | | |
| Pro | Asp | Met | Ala | Gln | Gly | Gly | Gly | Thr | Gln | Pro | Glu | Asn | Ile | Ser | Lys |
| | 850 | | | | 855 | | | | 860 | | | | |
| Ser | Leu | Ser | Phe | Ile | Lys | Asp | Tyr | Ile | Lys | Asn | Leu |
| 865 | | | | | 870 | | | | 875 | | |